United States Patent
Drexler et al.

(10) Patent No.: US 11,746,623 B2
(45) Date of Patent: Sep. 5, 2023

(54) SYSTEM AND METHOD TO CALIBRATE DIGITAL ROCK WETTABILITY

(71) Applicant: HALLIBURTON ENERGY SERVICES, INC., Houston, TX (US)

(72) Inventors: Santiago Gabriel Drexler, Rio de Janeiro (BR); Rafael March Castaneda Neto, Rio de Janeiro (BR); Xiaobo Nie, Richmond, TX (US); Jonas Toelke, Houston, TX (US); Milena Ferreira De Siqueira Lima, Rio de Janeiro (BR)

(73) Assignee: Halliburton Energy Services, Inc., Houston, TX (US)

( * ) Notice: Subject to any disclaimer, the term of this patent is extended or adjusted under 35 U.S.C. 154(b) by 73 days.

(21) Appl. No.: 17/585,925

(22) Filed: Jan. 27, 2022

(65) Prior Publication Data
US 2023/0235649 A1 Jul. 27, 2023

(51) Int. Cl.
E21B 49/02 (2006.01)
G01N 33/24 (2006.01)
E21B 43/08 (2006.01)
E21B 43/26 (2006.01)
E21B 43/20 (2006.01)

(52) U.S. Cl.
CPC ............ *E21B 43/082* (2013.01); *E21B 43/20* (2013.01); *E21B 43/26* (2013.01); *E21B 49/02* (2013.01)

(58) Field of Classification Search
CPC ......... E21B 49/02; E21B 25/00; G01N 15/00; G01N 33/24
See application file for complete search history.

(56) References Cited

U.S. PATENT DOCUMENTS

| | | | |
|---|---|---|---|
| 7,716,028 B2 * | 5/2010 | Montaron | G06F 30/23 702/6 |
| 8,081,802 B2 | 12/2011 | Dvorkin et al. | |
| 8,583,410 B2 | 11/2013 | Sisk et al. | |
| 9,285,301 B2 | 3/2016 | De Prisco et al. | |
| 10,043,274 B2 * | 8/2018 | Varslot | G06T 17/30 |
| 11,314,909 B2 * | 4/2022 | Rabbani | G06F 17/13 |
| 2012/0151998 A1 * | 6/2012 | Willberg | G01N 1/286 73/38 |
| 2012/0152547 A1 | 6/2012 | Hinkel | |

(Continued)

FOREIGN PATENT DOCUMENTS

| | | |
|---|---|---|
| CN | 107680131 A | 2/2018 |
| EP | 2732135 A2 | 5/2014 |

(Continued)

OTHER PUBLICATIONS

English abstract of CN107680131; retrieved from www.espacenet.com on Jan. 14, 2022.
Konstantinopoulos M. et al., abstract of "Effect of Mineralogy on Initial Wettability and Oil Recovery from Silica-containing Chalk", European Association of Geoscientists & Engineers, Conference Proceedings, 81st EAGE Conference and Exhibition 2019, Jun. 2019, vol. 2019, p. 1-5; https://doi.org/10.3997/2214-4609.201900956.

(Continued)

*Primary Examiner* — Kenneth L Thompson
(74) *Attorney, Agent, or Firm* — Polsinelli PC (57) ABSTRACT

A method is provided. Cells of a digital model of a formation are classified corresponding with one or more classes based on minerals and/or pore sizes. Wettability of the formation in the digital model is calibrated based on imbibition and/or drainage curves from physical experimentation for a rock sample and the one or more classes of the cells of the digital model.

20 Claims, 4 Drawing Sheets

(56) References Cited

U.S. PATENT DOCUMENTS

| | | | |
|---|---|---|---|
| 2012/0241149 A1* | 9/2012 | Chen | G01V 3/32 |
| | | | 324/303 |
| 2013/0018641 A1 | 1/2013 | Prisco et al. | |
| 2015/0034307 A1 | 2/2015 | Howard et al. | |
| 2016/0245950 A1 | 8/2016 | Ramsay | |
| 2016/0377521 A1 | 12/2016 | Wickramathilaka | |
| 2017/0132781 A1* | 5/2017 | Roth | G01N 15/08 |
| 2021/0080371 A1* | 3/2021 | Johns | G01N 15/0806 |
| 2022/0011465 A1 | 1/2022 | Kibodeaux | |
| 2022/0154067 A1* | 5/2022 | Okuno | C09K 8/68 |
| 2022/0207219 A1* | 6/2022 | Otomo | G06F 30/28 |
| 2022/0414303 A1* | 12/2022 | Shaik | G01N 23/046 |
| 2023/0137288 A1* | 5/2023 | Saxena | G06N 3/084 |
| | | | 382/109 |

FOREIGN PATENT DOCUMENTS

| | | |
|---|---|---|
| EP | 2801844 A2 | 11/2014 |
| WO | 2012118867 A2 | 9/2012 |
| WO | 2014025970 A1 | 2/2014 |

OTHER PUBLICATIONS

Al-Muthana Ahmed S. et al., "Wettability as a Function of Pore Size By NMR", International Symposium of the Society of Core Analysts; Aberdeen, Scotland, UK, Aug. 27-30, 2012; SCA2012-31.
International Search Report and Written Opinion for PCT application No. PCT/US2022/014336, dated Oct. 21, 2022, 9 pages.

* cited by examiner

SYSTEM AND METHOD TO CALIBRATE DIGITAL ROCK WETTABILITY

FIELD

The present disclosure relates to calibrating rock wettability. In particular, the present disclosure relates to calibrating rock wettability in a digital model by integrating data from physical experimentation.

BACKGROUND

Wellbores are drilled into the earth for a variety of purposes including tapping into hydrocarbon bearing formations to extract the hydrocarbons for use as fuel, lubricants, chemical production, and other purposes. Core samples may be collected from the wellbore to facilitate evaluation of subterranean reservoirs and formation fluids.

Reservoir wettability depends on complex rock-fluid and fluid-fluid interactions, and its characterization is a major challenge in the oil Industry. Reservoir rocks are heterogeneous and multimineral and hence present wettability variations that, in most cases, are not well represented by a uniform wettability scenario. Wettability is commonly input in reservoir models through relative permeability and capillary pressure curves, and its uncertainty carries important errors in dynamic modelling and production forecast.

BRIEF DESCRIPTION OF THE DRAWINGS

In order to describe the manner in which the advantages and features of the disclosure can be obtained, reference is made to embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

It should be understood at the outset that although illustrative implementations of one or more embodiments are illustrated below, the disclosed compositions and methods may be implemented using any number of techniques. The disclosure should in no way be limited to the illustrative implementations, drawings, and techniques illustrated herein, but may be modified within the scope of the appended claims along with their full scope of equivalents.

Unless otherwise specified, any use of any form of the terms "connect," "engage," "couple," "attach," or any other term describing an interaction between elements is not meant to limit the interaction to direct interaction between the elements and also may include indirect interaction between the elements described. In the following discussion and in the claims, the terms "including" and "comprising" are used in an open-ended fashion, and thus should be interpreted to mean "including, but not limited to . . . ". Reference to up or down will be made for purposes of description with "up," "upper," "upward," "upstream," or "uphole" meaning toward the surface of the wellbore and with "down," "lower," "downward," "downstream," or "downhole" meaning toward the terminal end of the well, regardless of the wellbore orientation. The various characteristics described in more detail below, will be readily apparent to those skilled in the art with the aid of this disclosure upon reading the following detailed description, and by referring to the accompanying drawings.

The present disclosure generally relates to calibrating wettability in reservoir models. Wettability is commonly input in reservoir models through relative permeability and capillary pressure curves, and its uncertainty carries important errors in dynamic modelling and production forecast. Therefore, tuning wettability input to realistic reservoir conditions is of paramount importance.

Digital Rock Analysis has been conventionally applied to obtain digital rock volumes and numerically simulate key controls that govern multiphase flow, such as relative permeability and capillary pressure curves. However, the correct input of wettability is a fundamental part of any digital rock analysis-based workflow to achieve representative results. This disclosure proposes a systematic method to calibrate rock wettability on a pore-by-pore basis using an integrated approach involving digital rock analysis and accelerated physical experimentation.

The conventional workflows rely on a single wettability parameter, such as contact angle, USBM, Amott or other wettability characterization data as input. The use of a single wettability parameter in pore-scale flow simulations results in rocks models that are unable to represent the complexity of some of the more challenging plays, such as multimineral carbonates or clay-rich sandstones among others. The method disclosed herein allows to tune one or more wettability parameters that best fit the imbibition capillary pressure obtained in the laboratory. Therefore, it improves the construction of digital rock models capable of simulating all wettability cases: water-wet, oil-wet, neutral-wet and the more complex mixed-wet rocks.

Figure 1:
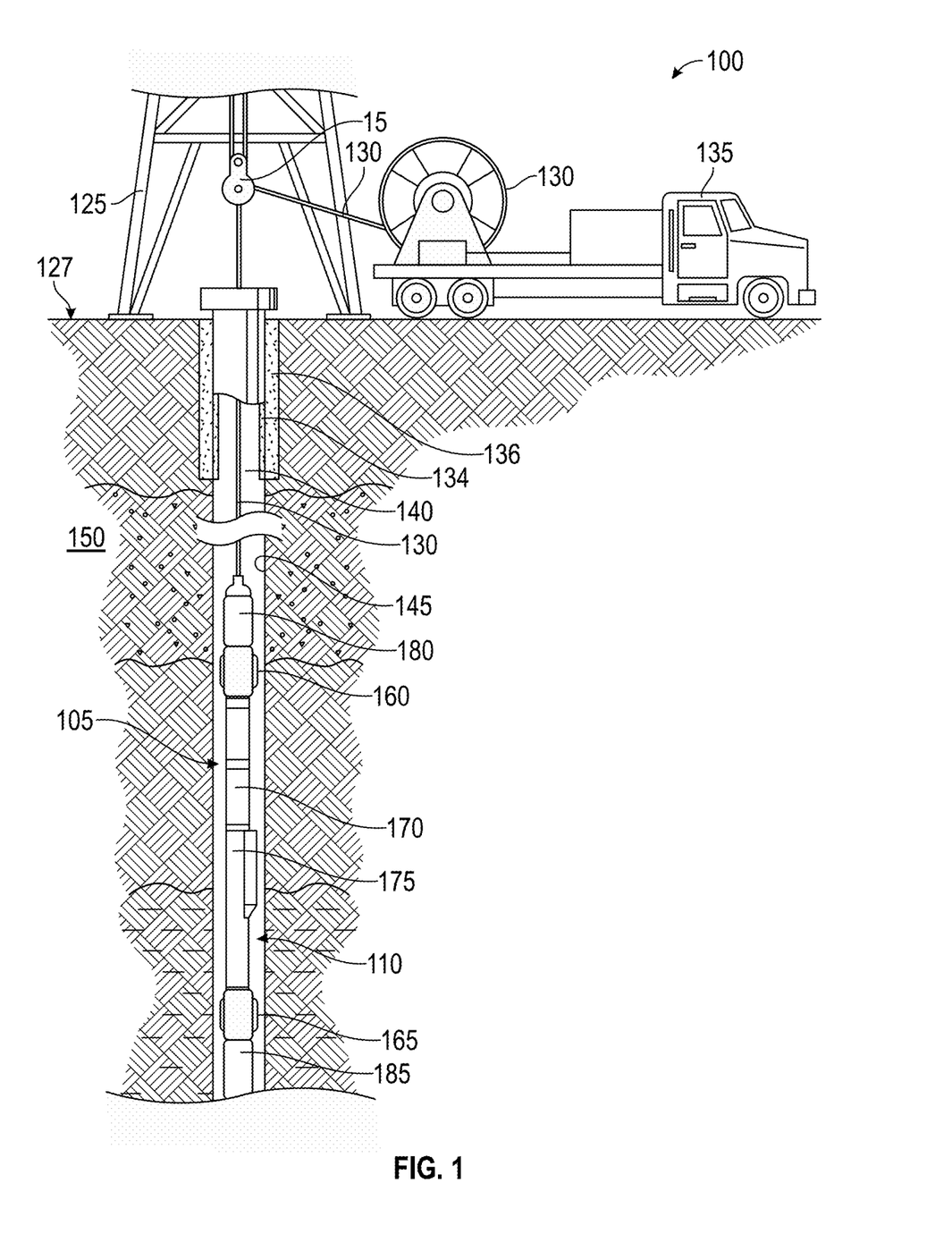
FIG. 1 is a schematic view of a wellbore operating environment in which a downhole core sampling apparatus may be deployed, according to an exemplary embodiment.

FIG. 1 illustrates a schematic view of an embodiment of a wellbore operating environment in which a downhole core sampling apparatus, method, and system may be deployed. As depicted, the operating environment 100 includes a derrick 125 that supports a hoist 115. Drilling oil and gas wells is commonly carried out using a string of drill pipes connected together so as to form a drilling string that is lowered through a rotary table into a wellbore 140. Here it is assumed that the drill string has been temporarily removed from the wellbore 140 to allow a downhole core sampling apparatus 105 to be lowered into the wellbore 140 that has been previously drilled through one or more formations 150.

As depicted, downhole core sampling apparatus 105 can be lowered into wellbore 140 by wireline conveyance 130 coupled with hoist 115. A casing 134 can be secured within the wellbore 140 by cement 136. The wireline conveyance 130 can be anchored to the derrick 125 or portable or mobile units such as a truck 135. The wireline conveyance 130 provides support for the downhole core sampling apparatus 105, as well as enabling communication between the downhole core sampling apparatus 105 and processors or controllers at the surface 127 outside the wellbore 140. The wireline conveyance 130 can be one or more wires, wireline, slickline, cables, tubulars, or the like. The wireline conveyance 130 can include fiber optic cabling or other wire or cable for carrying out communications. The optical cable can be provided internal or external of the conveyance 130. The wireline conveyance 130 is sufficiently strong and flexible to tether the downhole core sampling apparatus 105 through the wellbore 140, while also permitting communication through the wireline conveyance 130 to processors or controllers at the surface 127. Additionally, power can be supplied via the wireline conveyance 130 to meet the power requirements of the downhole core sampling apparatus 105. While a wireline conveyance 130 is illustrated in FIG. 1, other conveyances may be used to convey the core sampling apparatus 105 into the wellbore. In some instances, the core sampling apparatus 105 can be conveyed by wired coiled tubing.

As depicted in FIG. 1, the downhole core sampling apparatus 105 is lowered into wellbore 140 penetrating one or more formations 150 to a desired core sampling zone after which the downhole core sampling apparatus 105 may sample cores from the formation(s) 150, for example from the sidewall 145 of wellbore 140. The core sampling apparatus 105 can include an elongate housing 110, a first sealing element 160, a second sealing element 165, a sidewall coring tool 170, a core storage assembly 175, first pump 180, and second pump 185.

While FIG. 1 depicts a first sealing element 160 and a second sealing element 165, a downhole core sampling apparatus 105 that includes only a single sealing element is within the spirit and scope of the present disclosure. For instance, the downhole core sampling apparatus 105 may include only the first sealing element 160. In other cases, the downhole core sampling apparatus 105 may include only the second sealing element 165.

Although FIG. 1 depicts a vertical wellbore 140, the present disclosure is equally well-suited for use in wellbores having other orientations including horizontal wellbores, slanted wellbores, multilateral wellbores or the like. Also, even though FIG. 1 depicts an onshore operation, the present disclosure is equally well-suited for use in offshore operations.

FIG. 1 illustrates just one embodiment of a wellbore operating environment in which a downhole core sampling apparatus, method, and system may be deployed. The core sampling apparatus, method, and system may be deployed in other operating environments, such as a drilling environment. For instance, the core sampling apparatus 105 may be placed in a wellbore as part of a measurement while drilling (MWD) portion of a drillstring or as part of a logging while drilling (LWD) portion of a drillstring. In other instances, the core sampling apparatus 105 may be on a drillpipe as part of a wired drillpipe system.

Figure 2:
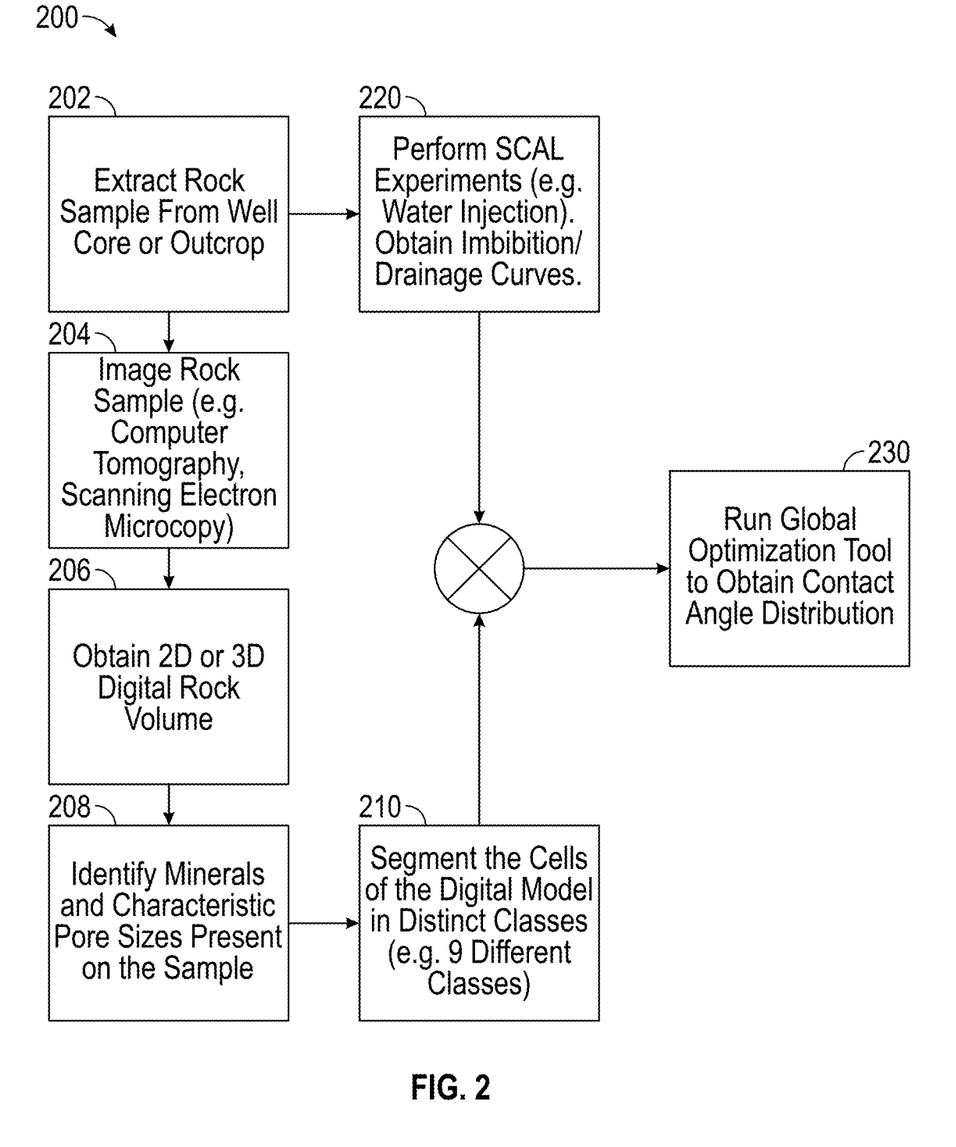
FIG. 2 is a flow chart of a process to calibrate wettability of a digital rock model.

Referring to FIG. 2, a flowchart is presented in accordance with an example embodiment. The method 200 is provided by way of example, as there are a variety of ways to carry out the method. The method 200 described below can be carried out using the configurations illustrated in FIGS. 1 and 3-5, for example, and various elements of these figures are referenced in explaining example method 200. Each block shown in FIG. 2 represents one or more processes, methods or subroutines, carried out in the example method 200. Furthermore, the illustrated order of blocks is illustrative only and the order of the blocks can change according to the present disclosure. Additional blocks may be added or fewer blocks may be utilized, without departing from this disclosure. The example method 200 can begin at block 202.

At block 202, a rock sample is obtained. In at least one example, the rock sample can be obtained from a well core and/or an outcrop. The rock sample can be extracted from a formation. For example, the rock sample can be obtained from a formation from which it is desired to extract oil. In some examples, the rock sample is obtained before drilling additional wellbores into the formation.

Figure 3:
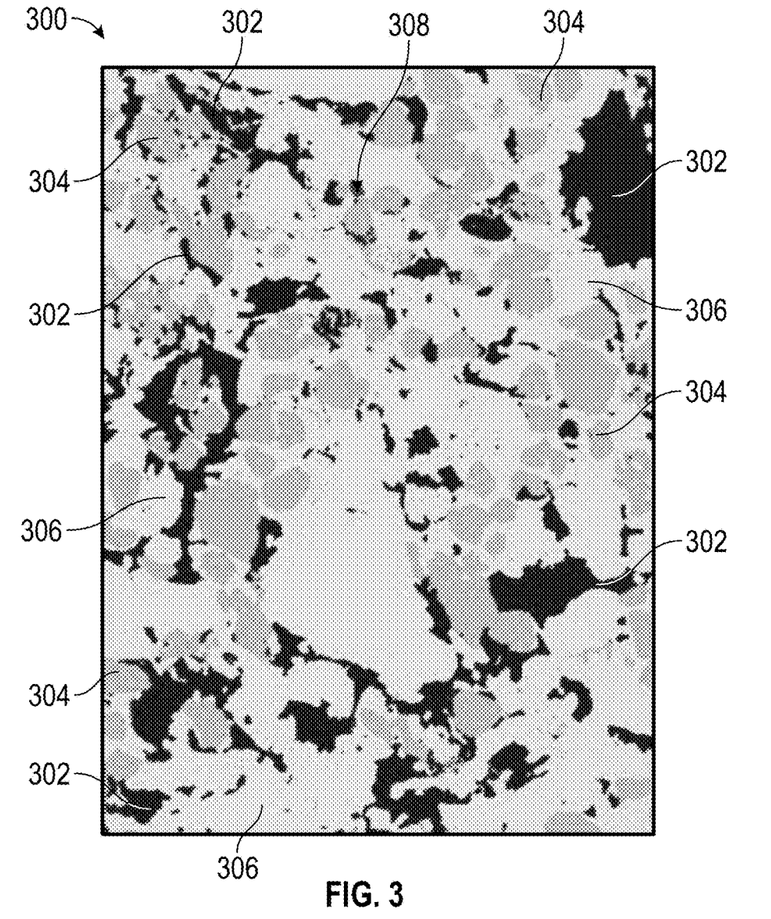
FIG. 3 is a diagram of a digital rock model.

At block 204, the rock sample is imaged. For example, the rock sample can be imaged by computer tomography, scanning electron microscopy, and/or any other suitable mechanism. At block 206, the two-dimensional and/or three-dimensional rock volume of the rock sample can be obtained. For example, FIG. 3 shows an example of a rock sample image 300. FIG. 3 shows a micro computer tomography image of a rock sample.

At block 208, minerals and/or pore sizes present on the sample can be identified. For example, as shown in FIG. 3, the rock sample image 300 shows a plurality of pores 302 present in the rock sample. The pores 302 can be openings the rock through which fluid can flow. The pores 302 may have different sizes and/or shapes. The size of each of the pores 302 may be calculated and/or estimated based on volume and/or area of the pore 302.

Each of the pores 302 are bordered by and/or adjacent to one or more minerals. For example, the minerals can include quartz 304, calcite 306, and/or pyrite 308. In some examples, other minerals may also be included in the rock sample 300. In some examples, only one type of mineral may be included in the rock sample 300.

At block 210, each of the cells of the digital model of the formation may be segmented or classified into one or more classes. The cells may be classified corresponding with one or more classes based on minerals and/or pore sizes. For example, cells with pore sizes within a first predetermined range may be classified into a first class, and cells with pore sizes within a second predetermined range may be classified into a second class. In some examples, cells with a first mineral (e.g., quartz) may be classified into a first class, and cells with a second mineral (e.g., calcite) may be classified into a second class. In some examples, the number of minerals and/or number of different minerals bordering a pore may be considered in classifying the cells. In some examples, the number of surfaces bordering the pore may be considered in classifying the cells.

In at least one example, the number of classes can be determined by a trained specialist. In some examples, the number of classes can be automated without human assistance.

At block 220, physical experimentation is performed on a rock sample from the formation. Based on the physical experimentation on the rock sample, the imbibition and/or drainage curves for the rock sample can be obtained. In some examples, the physical experimentation may have been performed in the past such that the data is historical data. In some examples, the physical experimentation may be performed prior to or at the same time as the development of the digital model and classifying the cells. With the historical data, the model can extend to any part of the reservoir and/or other wells that have similar properties or regions of interest. This can save a lot of time with calibrating models as more data is obtained. With the physical experimentation, an average behavior of rock wettability can be determined. While some data and parameters related to wettability can be determined through the physical experimentation, the physical experimentation alone cannot determine the wettability of the rock sample and/or formation pore-by-pore (e.g., for each pore and/or for each class of pores).

The physical experimentation can include special core analysis. The physical experimentation can include transient gas drainage, reservoir wettability restoration, spontaneous imbibition, and/or forced imbibition. In some examples, the physical experimentation can have a workflow such that draining transient gas is performed prior to restoring reservoir wettability, which can be performed prior to spontaneous imbibition, which can be performed prior to forced imbibition.

Transient gas drainage can include draining a clean brine-saturated sample under transient conditions in a porous plate experiment. For example, water can be drained from the rock by injecting gas. At a final saturation point, equilibrium can be reached to measure irreducible water saturation. This test can take between 3-4 weeks, as opposed to the 3-4 months for conventional porous plate experiments.

Reservoir wettability restoration can include flowing crude oil into the rock sample. In some examples, the crude oil can flow at irreducible water saturation conditions to establish rock-fluid interactions that govern wettability.

Spontaneous imbibition can include performing spontaneous imbibition using an oil-brine. In some examples, a gas-brine can be used for gas reservoirs. In some examples, spontaneous imbibition can be performed in an Amott cell.

Forced imbibition can include performing a centrifuge imbibition test using the same set of fluids as in the spontaneous imbibition test. The rotation speed can be calculated to ensure residual oil (or trapped gas) saturation is achieved. Forced imbibition can also be performed by flow experiments.

This physical experimentation workflow of transient gas drainage, reservoir wettability restoration, spontaneous imbibition, and/or forced imbibition provides the data needed to calibrate wettability for the digital model with a reduced timeline.

The digital special core analysis of the rock sample and/or formation can be performed with the digital model. The digital special core analysis can have a workflow that includes digital volume image acquisition and representative elementary volume definition, multiphase flow simulation, and wettability calibration. The multiphase flow simulation can be for gas primary drainage to quality control the representative elementary volume for multiphase flow using the results from the physical experimentation. The multiphase flow simulation can obtain relative permeability and/or capillary pressure simulated curves in the digital model.

At block 230, the wettability calibration can be performed by running drainage and/or imbibition numerical simulations using an optimization tool to find the optimal wettability parameter(s). Accordingly, the multiphase flow simulation and/or the wettability calibration can be performed via an optimization algorithm or tool implementing the data from the physical experimentation. The optimization tool can find the best wettability parameter(s) to match, within a predetermined threshold, the digital model with the spontaneous imbibition and/or forced imbibition results from the physical experimentation. Single or multiple parameters may be required depending on the complexity of the reservoir rock (e.g., presence of multiple minerals, heterogeneities, etc.).

The wettability calibration of the formation in the digital model can be based on imbibition and/or drainage curves from the physical experimentation for the rock sample and the one or more classes of the cells of the digital model. Calibrating wettability of the formation in the digital model can include determining one or more contact angles for each of the classes of the cells. The method can find the optimal distribution of wettability parameter(s) (e.g., contact angles) that minimizes the error between the experimental and the digital results. For example, calibrating wettability of the formation in the digital model can include adjusting the parameter(s) to decrease an error between the imbibition and/or drainage curves from the physical experimentation and the digital model. One or more wettability parameters can be adjusted until the digital model is within a predetermined range from spontaneous imbibition and/or forced imbibition from the physical experimentation.

Contact angle distribution can be determined for each class, as determined in block 210. For example, each surface or similar surfaces can have contact angle values. This provides better resolution for wettability calibration, instead of the conventional practice of only having a single contact angle value applied to the entire simulation.

In the example of FIG. 3, three contact angle values would need to be found via global optimization. As the pores 302 have different sizes, more contact angle values would need to be calibrated (e.g., separate the pore size range in four characteristic values, leading to twelve values—four size values times three phase values—to be found via optimization in total).

In at least one example, the wettability calibration can be carried out in a stochastic or deterministic mode. In the stochastic mode, two parameters (e.g., mean and standard deviation) can be optimized for each pore class. In the deterministic mode, a single parameter (e.g., mean) can be optimized for each pore class (e.g., assume the standard deviation equals zero). Accordingly, different scenarios can be considered:

Scenario 1: Pore-Size Dependent Contact-Angles
Pore size distribution discretizes the range of pore sizes into 'N' bins.
If two parameters (e.g., mean and standard deviation) are learned, two situations may apply:
1) Mean=unknown, standard deviation=0: The problem is deterministic for each pore size. Number of parameters is 'N': one mean contact angle for each pore size.
2) Mean=unknown, standard deviation=unknown. The problem is stochastic for each pore size. Number of parameters is '2N=N+N': one mean contact angle and one standard deviation contact angle for each pore size.

Scenario 2: Mineral-Dependent Contact-Angles
Mineralogy analysis finds 'M' minerals.
If two parameters (e.g., mean and standard deviation) are learned, two situations may apply:
1) Mean=unknown, standard deviation=0: The problem is deterministic for each mineral. Number of parameters is 'M': one mean contact angle for each mineral.
2) Mean=unknown, standard deviation=unknown. The problem is stochastic for each mineral. Number of parameters is '2M=M+M': one mean contact angle and one standard deviation contact angle for each mineral.

Scenario 3: Mineral and Pore-Size Dependent Contact-Angles

Mineralogy analysis finds 'N' minerals and Pore size distribution discretizes the range of pore sizes into 'N' bins.

If two parameters (e.g., mean and standard deviation) are learned, two situations may apply:

1) Mean=unknown, standard deviation=0: The problem is deterministic for each [mineral, pore-size] pair. Number of parameters is one mean contact angle for each [mineral, pore-size] pair.

2) Mean=unknown, standard deviation=unknown. The problem is stochastic for each [mineral, pore-size] pair. Number of parameters is '2 M*N=M*N+M*N': one mean contact angle and one standard deviation contact angle for each [mineral, pore-size] pair.

Figure 4:
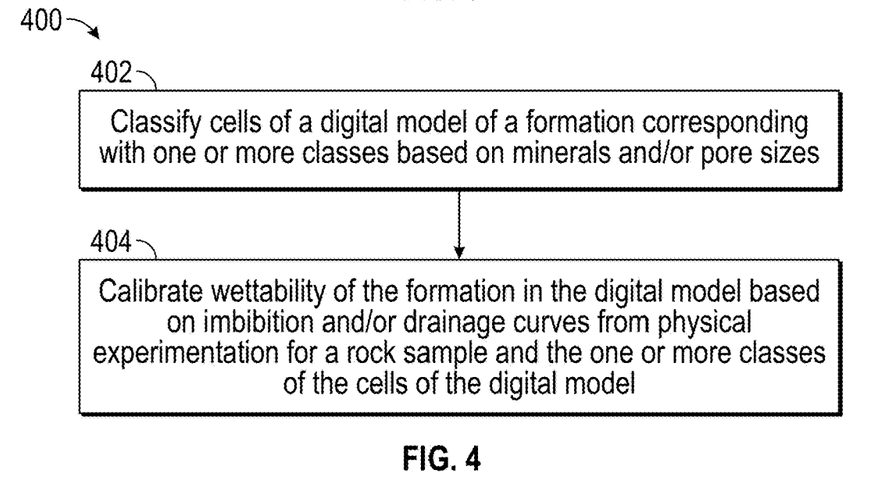
FIG. 4 is a flow chart of a method for calibrating wettability of a digital rock model.

Referring to FIG. 4, a flowchart is presented in accordance with an example embodiment. The method 400 is provided by way of example, as there are a variety of ways to carry out the method. The method 400 described below can be carried out using the configurations illustrated in FIGS. 1-3 and 5, for example, and various elements of these figures are referenced in explaining example method 400. Each block shown in FIG. 4 represents one or more processes, methods or subroutines, carried out in the example method 400. Furthermore, the illustrated order of blocks is illustrative only and the order of the blocks can change according to the present disclosure. Additional blocks may be added or fewer blocks may be utilized, without departing from this disclosure. The example method 400 can begin at block 402.

At block 402, cells of a digital model of a formation are classified corresponding with one or more classes based on minerals and/or pore sizes.

In at least one example, physical experimentation is performed on a rock sample. In some examples, the physical experimentation can include transient gas drainage, reservoir wettability restoration, spontaneous imbibition, and/or forced imbibition. In some examples, reservoir wettability restoration can include flowing crude oil into the rock sample.

In some examples, a multiphase flow simulation can be performed to obtain relative permeability and/or capillary pressure simulated curves in the digital model.

At block 404, wettability of the formation in the digital model is calibrated based on imbibition and/or drainage curves from the physical experimentation for the rock sample and the one or more classes of the cells of the digital model. In some examples, the calibrating wettability of the formation in the digital model can include determining one or more contact angles for each of the classes of the cells. In some examples, the calibrating wettability of the formation in the digital model can include decreasing an error between the imbibition and/or drainage curves from the physical experimentation and the digital model. In some examples, the calibrating wettability of the formation in the digital model can include adjusting one or more wettability parameters until the digital model is within a predetermined range from spontaneous imbibition and/or forced imbibition from the physical experimentation.

In at least one example, the imbibition and/or drainage curves for the rock sample can be obtained based on the physical experimentation on the rock sample.

Integrating the physical experimentation with the digital model as provided herein can reduce timelines at reduced cost, require only a small amount of material (e.g., no larger than 1 centimeter per sample), and allows for simulation of different flow conditions in the same volumes of rock. Additionally, the digital model is calibrated and the wettability can be calculated pixel by pixel or pore by pore. The increased resolution for wettability after calibrated by the disclosed method provides a better estimation of the formation's properties. Production can be estimated more accurately, and the improved models can better determine how to drill. Accordingly, after running the improved model with calibrated wettability at a finer resolution, the drilling and/or production operation can be adjusted to optimize the process. For example, a different region or path may be drilled and/or different proppants or fluids may be used.

As noted above, FIG. 5 illustrates an example computing device architecture 500 of a computing device, which can implement the various technologies and techniques described herein. The components of the computing device architecture 500 are shown in electrical communication with each other using a connection 505, such as a bus. The example computing device architecture 500 includes a processing unit (CPU or processor) 510 and a computing device connection 505 that couples various computing device components including the computing device memory 515, such as read only memory (ROM) 520 and random access memory (RAM) 525, to the processor 510.

Figure 5:
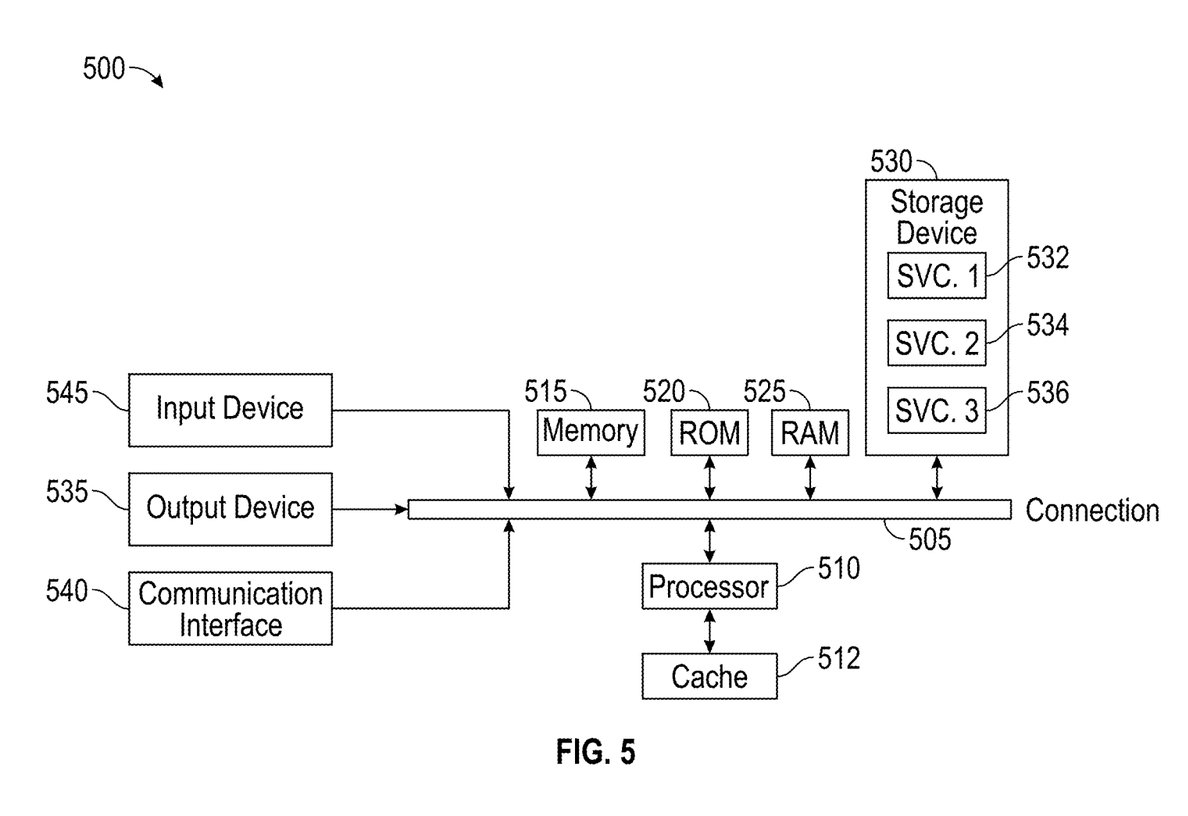
FIG. 5 illustrates an example computing device architecture that can be employed to perform various steps, methods, and techniques disclosed herein.

The computing device architecture 500 can include a cache of high-speed memory connected directly with, in close proximity to, or integrated as part of the processor 510. The computing device architecture 500 can copy data from the memory 515 and/or the storage device 530 to the cache 512 for quick access by the processor 510. In this way, the cache can provide a performance boost that avoids processor 510 delays while waiting for data. These and other modules can control or be configured to control the processor 510 to perform various actions. Other computing device memory 515 may be available for use as well. The memory 515 can include multiple different types of memory with different performance characteristics. The processor 510 can include any general purpose processor and a hardware or software service, such as service 1 532, service 2 534, and service 3 536 stored in storage device 530, configured to control the processor 510 as well as a special-purpose processor where software instructions are incorporated into the processor design. The processor 510 may be a self-contained system, containing multiple cores or processors, a bus, memory controller, cache, etc. A multi-core processor may be symmetric or asymmetric.

To enable user interaction with the computing device architecture 500, an input device 545 can represent any number of input mechanisms, such as a microphone for speech, a touch-sensitive screen for gesture or grail input, keyboard, mouse, motion input, speech and so forth. An output device 535 can also be one or more of a number of output mechanisms known to those of skill in the art, such as a display, projector, television, speaker device, etc. In some instances, multimodal computing devices can enable a user to provide multiple types of input to communicate with the computing device architecture 500. The communications interface 540 can generally govern and manage the user input and computing device output. There is no restriction on operating on any particular hardware arrangement and therefore the basic features here may easily be substituted for improved hardware or firmware arrangements as they are developed.

Storage device 530 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 525, read only memory (ROM) 520, and hybrids thereof. The storage device 530 can include services 532, 534, 536 for controlling the processor 510. Other hardware or software modules are contemplated. The storage device 530 can be connected to the computing device connection 505. In one aspect, a hardware module that performs a particular function can include the software component stored in a computer-readable medium in connection with the necessary hardware components, such as the processor 510, connection 505, output device 535, and so forth, to carry out the function.

As understood by those of skill in the art, machine-learning based classification techniques can vary depending on the desired implementation. For example, machine-learning classification schemes can utilize one or more of the following, alone or in combination: hidden Markov models; recurrent neural networks; convolutional neural networks (CNNs); deep learning; Bayesian symbolic methods; general adversarial networks (GANs); support vector machines; image registration methods; applicable rule-based system. Where regression algorithms are used, they may include including but are not limited to: a Stochastic Gradient Descent Regressor, and/or a Passive Aggressive Regressor, etc.

Machine learning classification models can also be based on clustering algorithms (e.g., a Mini-batch K-means clustering algorithm), a recommendation algorithm (e.g., a Miniwise Hashing algorithm, or Euclidean Locality-Sensitive Hashing (LSH) algorithm), and/or an anomaly detection algorithm, such as a Local outlier factor. Additionally, machine-learning models can employ a dimensionality reduction approach, such as, one or more of: a Mini-batch Dictionary Learning algorithm, an Incremental Principal Component Analysis (PCA) algorithm, a Latent Dirichlet Allocation algorithm, and/or a Mini-batch K-means algorithm, etc.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can include, for example, instructions and data, which cause or otherwise configure a general purpose computer, special purpose computer, or a processing device to perform a certain function or group of functions. Portions of computer resources used can be accessible over a network. The computer executable instructions may be, for example, binaries, intermediate format instructions such as assembly language, firmware, source code, etc. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can include hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are example means for providing the functions described in the disclosure.

In the foregoing description, aspects of the application are described with reference to specific embodiments thereof, but those skilled in the art will recognize that the application is not limited thereto. Thus, while illustrative embodiments of the application have been described in detail herein, it is to be understood that the disclosed concepts may be otherwise variously embodied and employed, and that the appended claims are intended to be construed to include such variations, except as limited by the prior art. Various features and aspects of the above-described subject matter may be used individually or jointly. Further, embodiments can be utilized in any number of environments and applications beyond those described herein without departing from the broader spirit and scope of the specification. The specification and drawings are, accordingly, to be regarded as illustrative rather than restrictive. For the purposes of illustration, methods were described in a particular order. It should be appreciated that in alternate embodiments, the methods may be performed in a different order than that described.

Where components are described as being "configured to" perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

The various illustrative logical blocks, modules, circuits, and algorithm steps described in connection with the examples disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present application.

The techniques described herein may also be implemented in electronic hardware, computer software, firmware, or any combination thereof. Such techniques may be implemented in any of a variety of devices such as general purposes computers, wireless communication device handsets, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the method, algorithms, and/or operations described above. The computer-readable data storage medium may form part of a computer program product, which may include packaging materials.

The computer-readable medium may include memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

Other embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Embodiments may also be practiced in distributed computing environments where tasks are performed by local and remote processing devices that are linked (either by hard-wired links, wireless links, or by a combination thereof) through a communications network. In a distributed computing environment, program modules may be located in both local and remote memory storage devices.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims. Moreover, claim language reciting "at least one of" a set indicates that a system including either one member of the set, or multiple members of the set, or all members of the set, satisfies the claim.

Statements of the Disclosure Include:

Statement 1: A method is disclosed comprising: classifying cells of a digital model of a formation corresponding with one or more classes based on minerals and/or pore sizes; and calibrating wettability of the formation in the digital model based on imbibition and/or drainage curves from physical experimentation for a rock sample and the one or more classes of the cells of the digital model.

Statement 2: A method is disclosed according to Statement 1, wherein the calibrating wettability of the formation in the digital model includes determining one or more contact angles for each of the classes of the cells.

Statement 3: A method is disclosed according to Statements 1 or 2, wherein the calibrating wettability of the formation in the digital model includes decreasing an error between the imbibition and/or drainage curves from the physical experimentation and the digital model.

Statement 4: A method is disclosed according to any of preceding Statements 1-3, wherein the calibrating wettability of the formation in the digital model includes adjusting one or more wettability parameters until the digital model is within a predetermined range from spontaneous imbibition and/or forced imbibition from the physical experimentation.

Statement 5: A method is disclosed according to any of preceding Statements 1-4, further comprising: obtaining the imbibition and/or drainage curves for the rock sample based on the physical experimentation on the rock sample.

Statement 6: A method is disclosed according to Statement 5, wherein the physical experimentation includes transient gas drainage, reservoir wettability restoration, spontaneous imbibition, and forced imbibition.

Statement 7: A method is disclosed according to Statement 6, wherein the reservoir wettability restoration includes flowing crude oil into the rock sample.

Statement 8: A method is disclosed according to any of preceding Statements 1-7, further comprising: performing a multiphase flow simulation to obtain relative permeability and/or capillary pressure simulated curves in the digital model.

Statement 9: A system is disclosed comprising: one or more processors; and a non-transitory computer-readable medium storing instructions that, when executed by the processors, cause the processors to perform operations comprising: classifying cells of a digital model of the formation corresponding with one or more classes based on minerals and/or pore sizes; and calibrating wettability of the formation in the digital model based on imbibition and/or drainage curves from physical experimentation for a rock sample and the one or more classes of the cells of the digital model.

Statement 10: A system is disclosed according to Statement 9, wherein the calibrating wettability of the formation in the digital model includes determining one or more contact angles for each of the classes of the cells.

Statement 11: A system is disclosed according to Statements 9 or 10, wherein the calibrating wettability of the formation in the digital model includes decreasing an error between the imbibition and/or drainage curves from the physical experimentation and the digital model.

Statement 12: A system is disclosed according to any of preceding Statements 9-11, wherein the calibrating wettability of the formation in the digital model includes adjusting one or more wettability parameters until the digital model is within a predetermined range from spontaneous imbibition and/or forced imbibition from the physical experimentation.

Statement 13: A system is disclosed according to any of preceding Statements 9-12, further comprising: obtaining the imbibition and/or drainage curves for the rock sample based on the physical experimentation on the rock sample.

Statement 14: A system is disclosed according to Statement 13, wherein the physical experimentation includes transient gas drainage, reservoir wettability restoration, spontaneous imbibition, and forced imbibition.

Statement 15: A system is disclosed according to Statement 14, wherein the reservoir wettability restoration includes flowing crude oil into the rock sample.

Statement 16: A system is disclosed according to any of preceding Statements 9-15, further comprising: performing a multiphase flow simulation to obtain relative permeability and/or capillary pressure simulated curves in the digital model.

Statement 17: A non-transitory computer-readable medium is disclosed comprising instructions, the instructions, when executed by one or more processors, cause the processors to perform operations comprising: classifying cells of a digital model of the formation corresponding with one or more classes based on minerals and/or pore sizes; and calibrating wettability of the formation in the digital model based on imbibition and/or drainage curves from physical experimentation for a rock sample and the one or more classes of the cells of the digital model.

Statement 18: A non-transitory computer-readable medium is disclosed according to Statement 17, wherein the calibrating wettability of the formation in the digital model includes determining one or more contact angles for each of the classes of the cells.

Statement 19: A non-transitory computer-readable medium is disclosed according to Statements 17 or 18, wherein the calibrating wettability of the formation in the digital model includes decreasing an error between the imbibition and/or drainage curves from the physical experimentation and the digital model.

Statement 20: A non-transitory computer-readable medium is disclosed according to any of preceding Statements 17-19, wherein the calibrating wettability of the formation in the digital model includes adjusting one or more wettability parameters until the digital model is within a predetermined range from spontaneous imbibition and/or forced imbibition from the physical experimentation.

What is claimed is:

1. A method comprising:
   classifying cells of a digital model of a formation corresponding with one or more classes based on minerals and/or pore sizes; and
   calibrating wettability of the formation in the digital model based on imbibition and/or drainage curves from physical experimentation for a rock sample and the one or more classes of the cells of the digital model.

2. The method of claim 1, wherein the calibrating wettability of the formation in the digital model includes determining one or more contact angles for each of the classes of the cells.

3. The method of claim 1, wherein the calibrating wettability of the formation in the digital model includes decreasing an error between the imbibition and/or drainage curves from the physical experimentation and the digital model.

4. The method of claim 1, wherein the calibrating wettability of the formation in the digital model includes adjusting one or more wettability parameters until the digital model is within a predetermined range from spontaneous imbibition and/or forced imbibition from the physical experimentation.

5. The method of claim 1, further comprising:
   obtaining the imbibition and/or drainage curves for the rock sample based on the physical experimentation on the rock sample.

6. The method of claim 5, wherein the physical experimentation includes transient gas drainage, reservoir wettability restoration, spontaneous imbibition, and forced imbibition.

7. The method of claim 6, wherein the reservoir wettability restoration includes flowing crude oil into the rock sample.

8. The method of claim 1, further comprising: performing a multiphase flow simulation to obtain relative permeability and/or capillary pressure simulated curves in the digital model.

9. A system comprising:
   one or more processors; and
   a non-transitory computer-readable medium storing instructions that, when executed by the processors, cause the processors to perform operations comprising:
      classifying cells of a digital model of the formation corresponding with one or more classes based on minerals and/or pore sizes; and
      calibrating wettability of the formation in the digital model based on imbibition and/or drainage curves from physical experimentation for a rock sample and the one or more classes of the cells of the digital model.

10. The system of claim 9, wherein the calibrating wettability of the formation in the digital model includes determining one or more contact angles for each of the classes of the cells.

11. The system of claim 9, wherein the calibrating wettability of the formation in the digital model includes decreasing an error between the imbibition and/or drainage curves from the physical experimentation and the digital model.

12. The system of claim 9, wherein the calibrating wettability of the formation in the digital model includes adjusting one or more wettability parameters until the digital model is within a predetermined range from spontaneous imbibition and/or forced imbibition from the physical experimentation.

13. The system of claim 9, further comprising:
   obtaining the imbibition and/or drainage curves for the rock sample based on the physical experimentation on the rock sample.

14. The system of claim 13, wherein the physical experimentation includes transient gas drainage, reservoir wettability restoration, spontaneous imbibition, and forced imbibition.

15. The system of claim 14, wherein the reservoir wettability restoration includes flowing crude oil into the rock sample.

16. The system of claim 9, further comprising: performing a multiphase flow simulation to obtain relative permeability and/or capillary pressure simulated curves in the digital model.

17. A non-transitory computer-readable medium comprising instructions, the instructions, when executed by one or more processors, cause the processors to perform operations comprising:
   classifying cells of a digital model of the formation corresponding with one or more classes based on minerals and/or pore sizes; and
   calibrating wettability of the formation in the digital model based on imbibition and/or drainage curves from physical experimentation for a rock sample and the one or more classes of the cells of the digital model.

18. The non-transitory computer-readable medium of claim 17, wherein the calibrating wettability of the formation in the digital model includes determining one or more contact angles for each of the classes of the cells.

19. The non-transitory computer-readable medium of claim 17, wherein the calibrating wettability of the formation in the digital model includes decreasing an error between the imbibition and/or drainage curves from the physical experimentation and the digital model.

20. The non-transitory computer-readable medium of claim 17, wherein the calibrating wettability of the formation in the digital model includes adjusting one or more wettability parameters until the digital model is within a predetermined range from spontaneous imbibition and/or forced imbibition from the physical experimentation.

* * * * *